United States Patent
Wieth et al.

(10) Patent No.: US 9,943,218 B2
(45) Date of Patent: Apr. 17, 2018

(54) ENDOSCOPE HAVING A SUPPLY CABLE ATTACHED THERETO

(71) Applicant: EndoChoice, Inc., Alpharetta, GA (US)

(72) Inventors: Stephan Wieth, Klein Nordende (DE); Alexander Lang, Wedel (DE)

(73) Assignee: ENDOCHOICE, INC., Alpharetta, GA (US)

( * ) Notice: Subject to any disclaimer, the term of this patent is extended or adjusted under 35 U.S.C. 154(b) by 575 days.

(21) Appl. No.: 14/500,975

(22) Filed: Sep. 29, 2014

(65) Prior Publication Data

US 2015/0094536 A1   Apr. 2, 2015

Related U.S. Application Data

(60) Provisional application No. 61/885,124, filed on Oct. 1, 2013, provisional application No. 61/900,134, filed on Nov. 5, 2013, provisional application No. 61/935,663, filed on Feb. 4, 2014, provisional application No. 61/936,688, filed on Feb. 6, 2014.

(30) Foreign Application Priority Data

Oct. 1, 2013 (DE) .................... 2013100112145300

(51) Int. Cl.
*A61B 1/04* (2006.01)
*A61B 1/00* (2006.01)

(52) U.S. Cl.
CPC ....... *A61B 1/00124* (2013.01); *A61B 1/00112* (2013.01); *A61B 1/00114* (2013.01)

(58) Field of Classification Search
CPC ............ A61B 1/00112; A61B 1/00114; A61B 1/00117; A61B 1/00119; A61B 1/00121; A61B 1/00124; A61B 1/00126–1/00127
USPC ........................................................ 600/132
See application file for complete search history.

(56) References Cited

U.S. PATENT DOCUMENTS

| | | |
|---|---|---|
| 3,639,714 A | 2/1972 | Fujimoto |
| 3,955,064 A | 5/1976 | Demetrio |
| 4,027,697 A | 6/1977 | Bonney |

(Continued)

FOREIGN PATENT DOCUMENTS

| | | |
|---|---|---|
| CA | 2297986 | 3/1999 |
| CA | 2765559 | 12/2010 |

(Continued)

OTHER PUBLICATIONS

Corrected Notice of Allowance dated Apr. 13, 2016 for U.S. Appl. No. 13/680,646.

(Continued)

*Primary Examiner* — Matthew J Kasztejna
(74) *Attorney, Agent, or Firm* — Bookoff McAndrews, PLLC

(57) ABSTRACT

The present specification describes a medical endoscope, such as but not limited to a gastroscope, a colonoscope or a bronchoscope. In particular, the present specification describes an endoscope having a supply cable that includes a coupling element dividing the supply cable into a first section and a second section capable of rotating relative to each other, wherein the endoscope system further includes a control unit or endoscope handle and a main connector or supply plug connected to opposite ends of the supply cable.

18 Claims, 8 Drawing Sheets

(56) References Cited

U.S. PATENT DOCUMENTS

| | | |
|---|---|---|
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | Ebbesmeiernee Schitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 * | 2/2003 | Ikeda ............... A61B 1/00121 600/110 |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |

(56) References Cited

U.S. PATENT DOCUMENTS

| | | |
|---|---|---|
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1* | 5/2006 | Boutillette ......... A61B 1/00128 600/136 |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 9/2008 | Seibel |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |

(56) References Cited

U.S. PATENT DOCUMENTS

| | | |
|---|---|---|
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2009-285304 A | 12/2009 |
| JP | 2010178766 A | 8/2010 |
| JP | 2012135432 | 7/2012 |
| JP | 2013116277 A2 | 6/2013 |
| JP | 2013123647 | 6/2013 |

(56) References Cited

FOREIGN PATENT DOCUMENTS

| | | |
|---|---|---|
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
International Search Report for PCT/US2014/58143, dated Jan. 21, 2015.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action dated Feb. 26, 2016 for U.S. Appl. No. 14/274,323.
Office Action dated Feb. 4, 2016 for U.S. Appl. No. 14/271,234.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.

(56) References Cited

OTHER PUBLICATIONS

Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.

\* cited by examiner

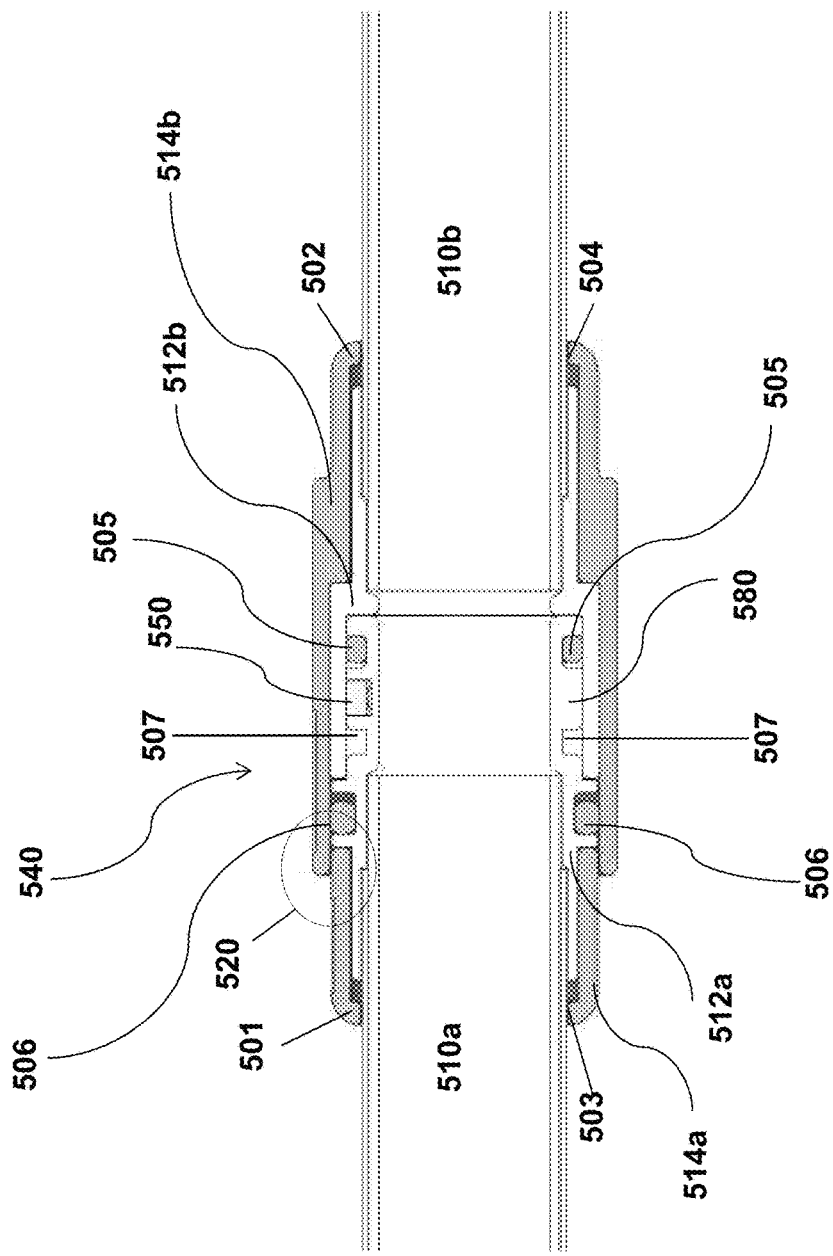

ENDOSCOPE HAVING A SUPPLY CABLE ATTACHED THERETO

CROSS-REFERENCE TO RELATED APPLICATIONS

The present specification relies upon German Provisional Patent Application Number 2013100112145300, entitled "Endoskop mit einem am Endoskop befestigten Versorgungskabel" and filed on Oct. 1, 2013; U.S. Provisional Patent Application No. 61/885,124, of the same title and filed on Oct. 1, 2013; U.S. Provisional Patent Application No. 61/900,134, of the same title and filed on Nov. 5, 2013; U.S. Provisional Patent Application No. 61/935,663, of the same title and filed on Feb. 4, 2014; and U.S. Provisional Patent Application No. 61/936,688, of the same title and filed on Feb. 6, 2014, for priority. All of the above-mentioned applications are herein incorporated by reference in their entirety.

FIELD

The present specification relates to a medical endoscope, such as a gastroscope, a colonoscope or a bronchoscope. In particular, the present specification relates to an endoscope having an umbilical/supply cable with a control unit attached at one end of the cable and a main connector (or supply plug) attached at the other end of the cable.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

The endoscopes are connected to a control unit via a supply cable. When handling such endoscopes, there exists the problem that on account of a rotation of the control unit the supply cable is twisted and the conductors running in the supply cable are therefore exposed to an increased level of stress. U.S. Pat. No. 6,520,908, dated Feb. 18, 2003 and assigned to Olympus Optical Co., Ltd. suggests a coupling that is provided on the control unit and on which the supply cable is articulated so that it can rotate to a certain extent, however, is fastened on its supply plug.

Even though this design provided in the cited prior art minimises the risk of torsions, when the operator reaches the maximum rotation, a feeling of strain arises which can have a very tiring effect on the operator. At the same time strong forces are produced which act on the coupling and the supply cable and may have to be countered by a corresponding design or reinforcement of the control unit, which again however reduces the operational convenience.

It is therefore the object of the present specification to provide a simple solution for avoiding torsions of the supply cable that stresses the operator of endoscopes as little as possible.

SUMMARY

The present specification discloses an endoscope having a supply cable comprising: a coupling element dividing the supply cable into a first section and a second section capable of rotating relative to each other, wherein the endoscope further comprises a control unit or endoscope handle and a main connector or supply plug connected to opposite ends of the supply cable.

Optionally, the supply cable comprises a coupling element dividing the supply cable into a first section and a second section, each section having a proximal end and a distal end, capable of rotating relative to each other, wherein the endoscope may further comprise a control unit and a main connector each connected to the distal ends of the supply cable sections. Still optionally, the coupling element comprises a first coupler component having a first end and a second end and a second coupler component having a first end and a second end. Still optionally, the diameter of the first end of the second coupler component is greater than the diameter of the second end of the first coupler component, the first and the second coupler components being coupled by inserting the second end of the first coupler component into the first end of the second coupler component.

Still optionally, the first coupler component includes a groove running around at least a portion of the circumference of the coupler component and a carriage movable in the groove, wherein an end of the second section of the supply cable is coupled to the carriage via the second coupler component. Optionally, the groove further comprises a limitation means that limits the rotatability of the first and the second sections of the supply cable relative to each other.

Optionally, the first section and the second section of the supply cable are equal in length.

In some embodiments, the present specification is directed toward an endoscope supply cable comprising: a first section of the supply cable, wherein the first section has a length of at least 10 centimeters, a first end and a second end; a second section of the supply cable, wherein the second section has a length of at least 10 centimeters, a first end and a second end; a coupling element for connecting the first end of the first section with the second end of the second section, wherein the coupling element is configured to enable the first section to rotate relative to the second section and wherein the coupling element further comprises: a first coupling component attached to the first end of the first section; a second coupling component attached to the second end of the second section; a groove extending around at least a portion of an outer periphery of the first coupling component; and a carriage configured to be movable in said groove, wherein the carriage is coupled to the second coupling component.

Optionally, the groove may be located within a rotator component that is positioned concentrically around the outer periphery of the first coupling component.

In some embodiments, the first and the second coupling components may be substantially cylindrical in shape.

In some embodiments, a diameter of a portion of the second coupling component is greater than a diameter of a portion of the first coupling component, the first and the second coupling components being coupled by inserting said smaller diameter end of the first coupling component into said larger diameter end of the second coupling component.

Optionally, the supply cable may further comprise a fastening mechanism inserted radially into at least one of the first and second coupling components through one or more openings in a wall of at least one of the first or second sections of the supply cable and fastened to one or more threaded holes using a fastening means. Optionally, the fastening means are screws.

Optionally, the supply cable may further comprise a limitation means that limits an angle of rotation of the first and the second sections of the supply cable relative to each other.

In some embodiments, the coupling element may further comprise a first o-ring seal and a second o-ring seal placed in alignment with a predetermined gap separating the first and the second o-ring seals, the first and the second o-ring seals enabling the first and the second sections of the supply cable to be rotatably connected while preventing contaminants from entering the endoscope.

Optionally, the first o-ring seal is placed near the second end of the second section of the supply cable and wherein the second o-ring is placed near the first end of the first section of the supply cable.

Optionally, the first section and the second section of the supply cable may be equal in length. Still optionally, the ratio of the lengths of the first to the second section may be one of 50:50, 40:60, 30:70, 20:80, 10:90, 45:55, 35:65, and 25:75.

In some embodiments, the coupling element and at least a portion of the first and second sections of the supply cable may be covered with a cover for preventing contaminants from entering the endoscope.

In some embodiments, the present specification describes an endoscope system comprising an endoscope, a main controller, and a supply cable adapted to connect the endoscope to the main controller comprising: a first section of the supply cable, wherein the first section has a length of at least 10 centimeters, a first end, and a second end configured to attach to the main controller; a second section of the supply cable, wherein the second section has a length of at least 10 centimeters, a first end configured to attach to the endoscope, and a second end; a coupling element for connecting the first end of the first section with the second end of the second section, wherein the coupling element is configured to enable the first section to rotate relative to the second section and wherein the coupling element further comprises: a first coupling component attached to the first end of the first section; a second coupling component attached to the second end of the second section; a groove extending around at least a portion of an outer periphery of the first coupling component; and a carriage configured to be movable in said groove, wherein the carriage may be coupled to the second coupling component; wherein the ratio of the lengths of the first and second sections may be one of 50:50, 40:60, 30:70, 20:80, 10:90, 45:55, 35:65, and 25:75.

Optionally, the first section and the second section of the supply cable are equal in length.

Optionally, the groove is located within a rotator component that is positioned concentrically around the outer periphery of the first coupling component.

Optionally, the first and the second coupling components are cylindrical in shape.

Optionally, a diameter of a portion of the second coupling component is greater than a diameter of a portion of the first coupling component, the first and the second coupling components being coupled by inserting said smaller diameter end of the first coupling component into said larger diameter end of the second coupling component.

In some embodiments, the system further comprises a fastening mechanism inserted radially into at least one of the first and second coupling components through one or more openings in a wall of at least one of the first and second sections of the supply cable and fastened to one or more threaded holes. Optionally, a fastening means, such as screws, are employed.

Optionally, the endoscope further comprises a limitation means that limits an angle of rotation of the first and the second sections of the supply cable relative to each other.

In some embodiments, the coupling element may further comprise a first o-ring seal and a second o-ring seal placed in alignment with a predetermined gap separating the first and the second o-ring seals, the first and the second o-ring seals enabling the first and the second sections of the supply cable to be rotatably connected while preventing contaminants from entering the endoscope.

Optionally, the first o-ring seal is placed near the second end of the second section of the supply cable and wherein the second o-ring is placed near the first end of the first section of the supply cable.

Optionally, the coupling element and at least a portion of the first and second sections of the supply cable may be covered with a cover for preventing contaminants from entering the endoscope.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 5 shows a cross-sectional view through a coupler component of the supply cable, in accordance with another embodiment of the present specification.

DETAILED DESCRIPTION

Figure 1A:
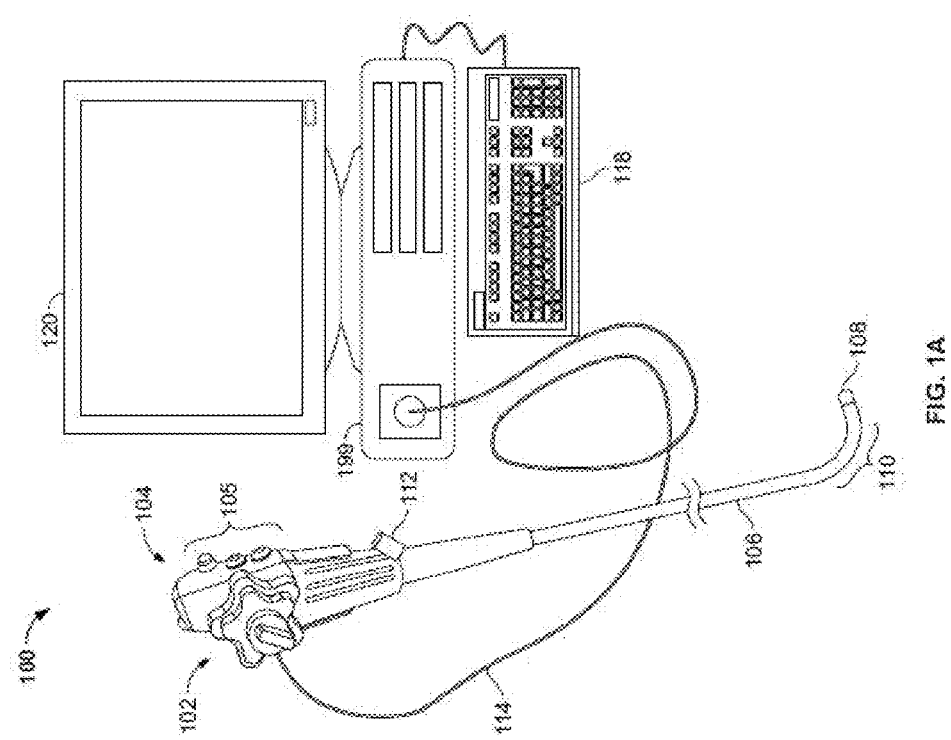
FIG. 1A shows a semi-pictorial view of an endoscopy system, according to some embodiments.

The present specification describes a device and method for reducing torsion in a supply (also known as umbilical)

cable attached to a control unit of an endoscope, thereby reducing the stress experienced by the endoscope operator during a procedure. In an embodiment, a first end of the supply cable is attached to a control unit and a second end to a supply plug. The supply cable is further equipped with a coupling that subdivides the supply cable into two sections that can be rotated relative to each other. When the supply cable is divided into two sections, each section has a distal end (connected to either the control unit or supply plug) and a proximal end (rotatably connected to one another via a rotational coupling).

The flexible properties of the supply cable described in the present specification are exploited for the "excessive rotational" properties of the coupling. According to an embodiment of the present specification, with the use of the coupling dividing the supply cable into two sections, the "excessive rotation", on account of the flexibility of the supply cable and the distance between the control unit and the coupling, does not have such a strong effect on the operation as exhibited in prior art, and is thus, not prohibited by torsion of the supply cable.

To form the coupling, it is provided that the supply cable is divided into at least two sections—a first section and a second section. The first section has both a proximal end and a distal end, having at its proximal end a groove that runs around the circumference of the first section, and a carriage that can move in the groove. In various embodiments, a groove is a channel, indentation, or space for receiving a structure; and a carriage is any member, protrusion, flange, etc. capable of being received into, and of moving within, the groove. The second section also has both a distal end and a proximal end, where the proximal end of the second section of the supply cable is attached to the carriage.

The proximal end of the second section is preferably drawn over the proximal end of the first section and exhibits an opening made through the wall of the proximal end of the second section for receiving a fastening means that is connected to the carriage.

Since there is a distance between the coupling and the supply plug, the entire supply cable is not rotated during operation, as in the case of conventional designs where a rotating coupling is directly provided on the supply plug portion.

There is also provided a limiting means that limits the rotation of the two sections of the supply cable with respect to each other, in order to avoid torsion which may damage the conductors and ducts that run through the supply cable. For example, the limiting means may comprise a groove that runs around only a portion of the circumference of the proximal end of the first section of the supply cable, and not around the entire circumference. The limiting means may also comprise providing a body that prevents the movement of the carriage that is introduced into the groove. In an embodiment, the limiting means are arranged such that a twisting of the two sections of the supply cable relative to each other is possible only up to a maximum of 360 degrees.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

Reference is now made to FIG. 1A, which shows a multiple viewing elements endoscopy system 100. System 100 may include a multiple viewing elements endoscope 102. Multiple viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted as well as one and more side service channel openings.

A supply cable 114, also referred to as an umbilical tube, may connect between handle 104 and a main control unit 199. In an embodiment, supply cable 114 has a first end connected with handle 114 and a second end connected with the main control unit 199. Supply cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1A, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system. Optionally, the video streams received from the different viewing elements of the multi-viewing element endoscope 102 may be displayed separately on at least one monitor (not seen) by uploading information from the main control unit 199, either side-by-side or interchangeably (namely, the operator may switch between views from the different viewing elements manually).

Figure 1B:
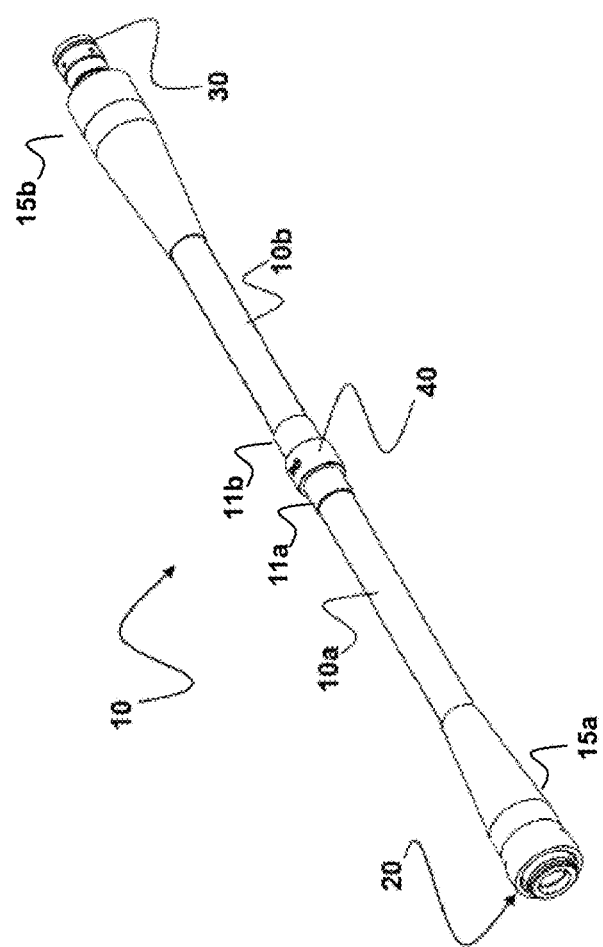
FIG. 1B shows a perspective view of a supply cable for an endoscope, in accordance with an embodiment of the present specification.

FIG. 1B shows a perspective view of a novel supply cable of an endoscope in accordance with an embodiment of the present specification. The supply cable 10 (also known as an umbilical tube or cable) comprises a coupling fastener 40 that subdivides the supply cable 10 into two sections—first section 10a and second section 10b. Section 10a has a first end 11a and a second end 15a. Section 10b also has a first end 15b and a second end 11b. Proximal ends 11a (first end of first section 10a) and 11b (second end of second section 10b) of sections 10a and 10b, respectively, are coupled with coupling fastener 40. In one embodiment, sections 10a and 10b are of equal length. In some embodiments, sections 10a and 10b may be of different lengths. For example, the relative lengths of the two sections 10a and 10b may be, but is not limited to, ratios (10a:10b) such as 50:50, 40:60, 30:70, 20:80, 10:90, 45:55, 35:65, or 25:75. Similarly, in some embodiments, the ratios of length of section 10b to 10a may be, but is not limited to 50:50, 40:60, 30:70, 20:80, 10:90, 45:55, 35:65, or 25:75. In various embodiments, a minimum length of sections 10a and section 10b range between 10 to 15 centimeters. A distal or second end 15a of section 10a is coupled with a first terminal 20 provided for connecting the supply cable 10 to a supply plug also known as a main connector unit, which is further connected to a handle portion of an endoscope. A distal or first end 15b of section 10b is coupled with a second terminal 30 provided for connecting the supply cable 10 to a main control unit. In various embodiments, terminals 20 and 30 are designed to rotate with respect to the supply cable 10. In various embodiments, the coupling fastener 40 allows a twisting of the first section 10a relative to the second section 10b at their proximal ends 11a and 11b, respectively.

Figure 1C:
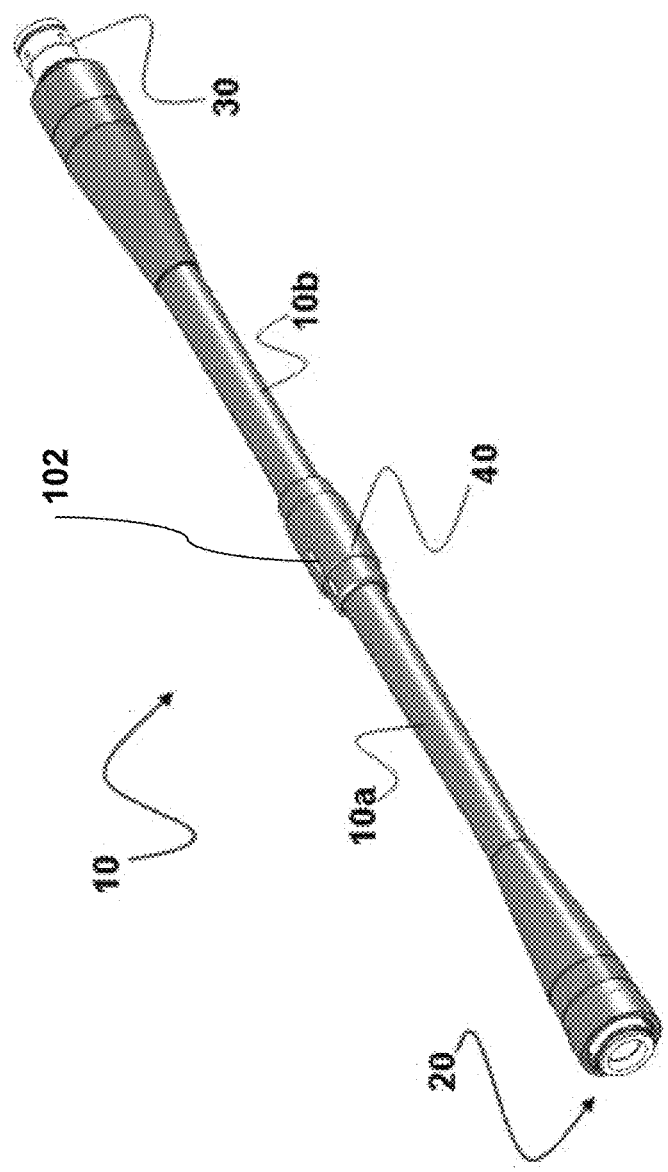
FIG. 1C shows a perspective view of a supply cable for an endoscope, in accordance with an embodiment of the present specification.

FIG. 1C shows a perspective view of a supply cable of an endoscope in accordance with another embodiment of the present specification. In addition to the parts of the supply cable 10 described in conjunction with FIG. 1B, the embodiment of supply cable 10 shown in FIG. 1C comprises a mark 102 on the coupling fastener 40. In an embodiment, a user may use the mark 102 to obtain a direction of orientation of the coupling fastener 40 with respect to the sections 10a and 10b of the supply cable 10 for connecting the same.

The design of the coupling fastener 40, in accordance with an embodiment of the present specification is described in detail with reference to FIGS. 2A, 2B, and 3-5.

Figure 2A:
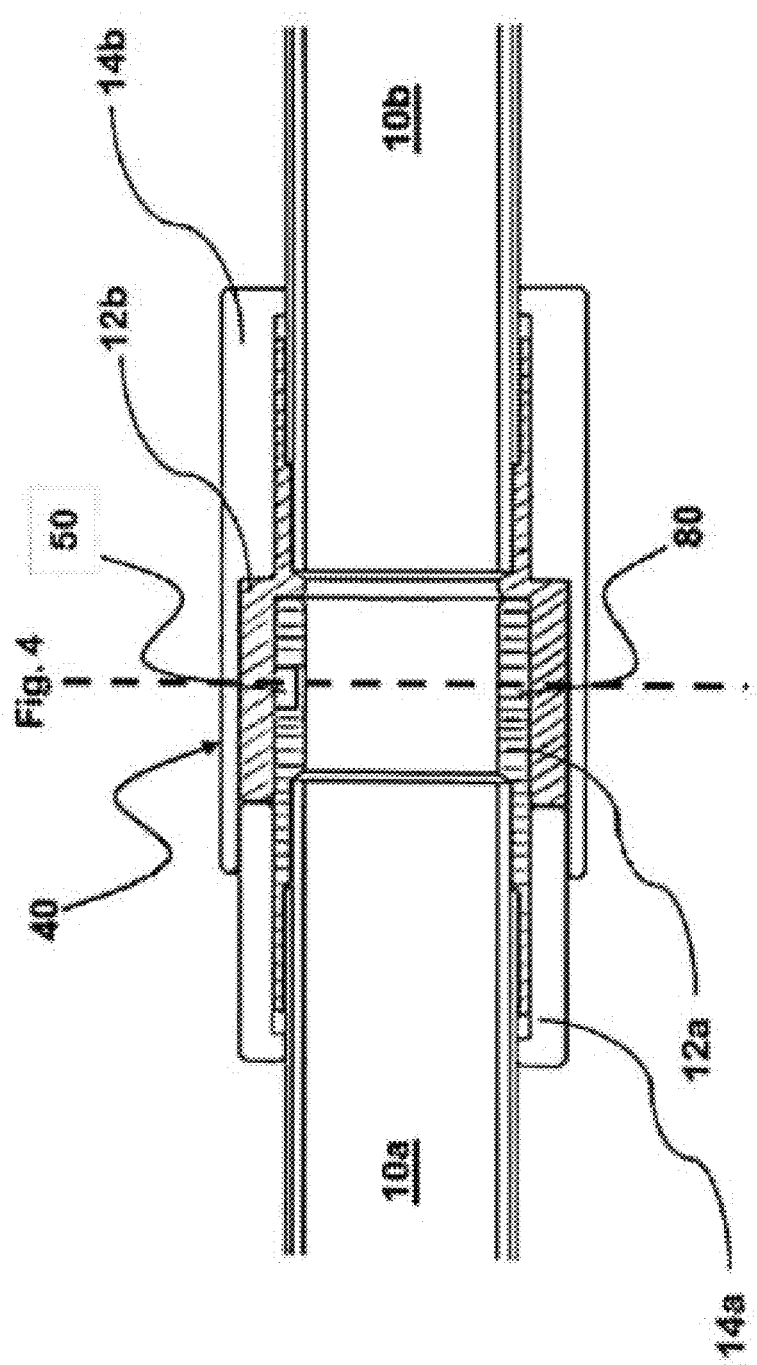
FIG. 2A shows a cross-sectional view of a coupling of the supply cable, in accordance with an embodiment of the present specification.

FIG. 2A shows a cross-sectional view through a coupling of the supply cable, in accordance with an embodiment of the present specification. Coupling fastener 40 comprises a first coupler component 12a and a second coupler component 12b. FIG. 2A further shows a first end of the first coupler component 12a coupled with a proximal end 11a of the section 10a. In various embodiments, coupler components 12a and 12b are cylindrical in shape having a hollow interior region. In the embodiment shown, the first and second coupler components 12a, 12b are shaped similar to a pipe. A second end of the first coupler component 12a is coupled with a first end of the second coupler component 12b, while a second end of the second coupler component 12b is coupled with a proximal end 11b of the section 10b. In an embodiment, the diameter of the first end of the second coupler component 12b is larger than that of the second end of the first coupler component 12a. In order to connect the two coupler components 12a, 12b, the second end of the first coupler component 12a is pushed into the first end of the second coupler component 12b. Hence, when in operation, as shown in the figure, a portion of coupler component 12a is inserted into at least a portion of coupler component 12b, to ensure a secure connection. Further, in an embodiment, there is no gap between the outer walls of the portion of coupler component 12a inserted into coupler component 12b and the inner walls of coupler component 12b.

To protect the coupling fastener 40 during cleaning processes and to maintain the integrity of the coupling fastener 40, a cover 14a, typically made of a material such as plastic, is fixed over at least a portion of section 10a and at least a portion of the coupler component 12a which is not inserted into coupler component 12b, as shown in the figure. Similarly, a cover 14b, typically made of a material such as plastic is fixed above a portion of the section 10b, the coupler component 12b and a portion of cover 14a, also as shown in FIG. 2A. In some embodiments, the length of cover 14b is greater than the length of cover 14a. In various embodiments, the cover 14a, 14b may be made of any durable water proof material such as rubber, metal, etc.

Further, a groove 50 is drilled in at least a portion of the outer periphery of coupler component 12a. The groove 50 is placed in a rotator portion 80 of the coupling fastener 40. The rotator portion 80 is shaped like a pipe and is, in one embodiment, concentric to coupler component 12a. As described in greater detail below with respect to FIG. 3, a carriage is introduced into the groove 50, via coupler component 12a, such that the carriage can move along the groove. The pipe-like shape of rotator portion 80 enables a 360 degrees rotation of the carriage along the groove 50.

Figure 2B:
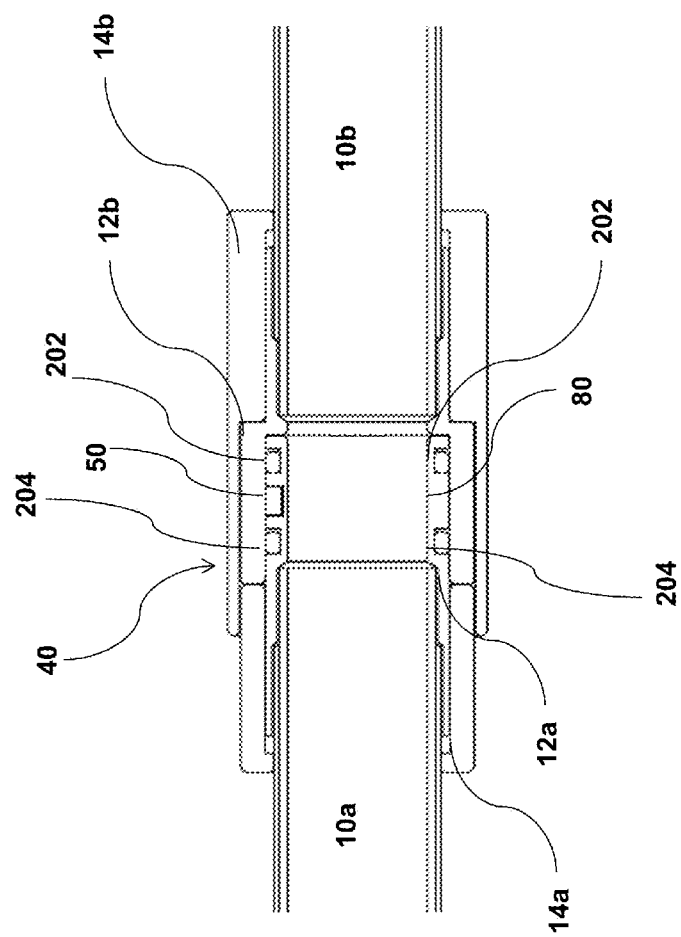
FIG. 2B shows a cross-sectional view of a coupling of the supply cable, in accordance with an embodiment of the present specification.

FIG. 2B shows a cross-sectional view through a coupling of the supply cable, in accordance with another embodiment of the present specification. In addition to the parts of the supply cable 10 and coupling fastener 40 described in conjunction with FIG. 2A, in one embodiment of the present specification, as shown in FIG. 2B, coupler component 12a further comprises a first o-ring 202 and a second o-ring 204. First o-ring 202 is fitted on coupler component 12a near the proximal end 11b of section 10b. Second o-ring 204 is fitted on coupler component 12b near the proximal end 11a of section 10a. As can be seen in FIG. 2B, first and second o-rings 202, 204 are positioned on coupler component 12b in a manner such that groove 50 is positioned between the two o-rings 202 and 204.

As is commonly known in the art, an o-ring is also known as a packing, or a toric joint, and is a mechanical gasket in the shape of a torus. More specifically, an o-ring is a loop of a material, typically an elastomer, with a disc-shaped cross-section, designed to be seated in a groove and compressed during assembly between two or more parts, thereby creating a seal at the interface of the two or more parts. An o-ring may be used in static or dynamic applications where there is relative motion between the parts and the o-ring. O-rings can seal large magnitudes of pressure.

The o-rings 202 and 204 are used as seals in coupling fastener 40 as the o-ring seals allow for a high local stress. The use of two o-ring seals 202 and 204 placed in an aligned position with a predetermined gap separating the seals enables proximal sections 10a and 10b of the supply cable 10 to be connected to the coupling fastener 40 with reduced force, while still maintaining a high seal pressure. In addition, the o-rings 202, 204 prevent any contaminants from entering the endoscope by providing an air tight seal.

Figure 3:
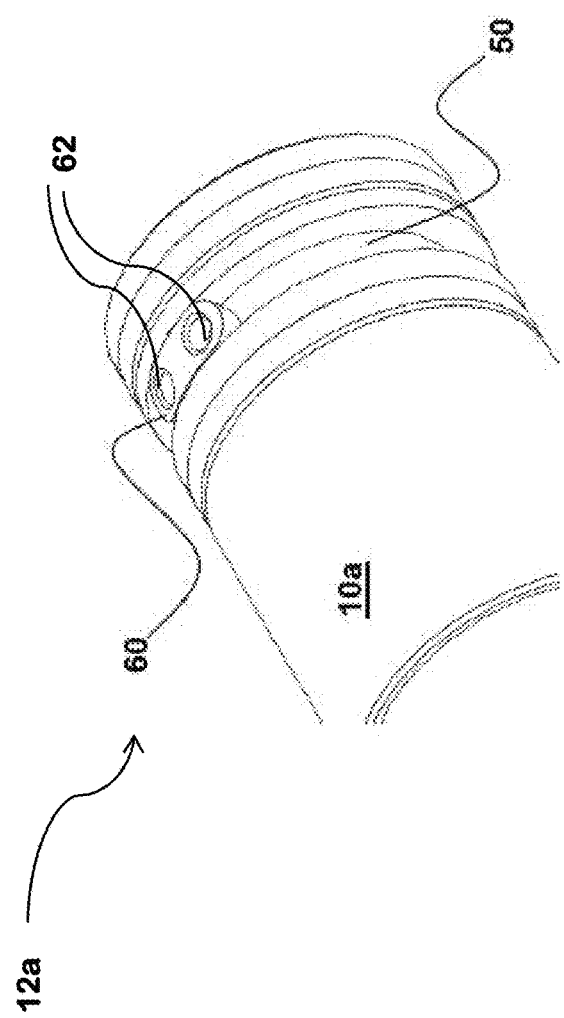
FIG. 3 shows a perspective view of a first section of the supply cable, in accordance with an embodiment of the present specification.
Figure 4:
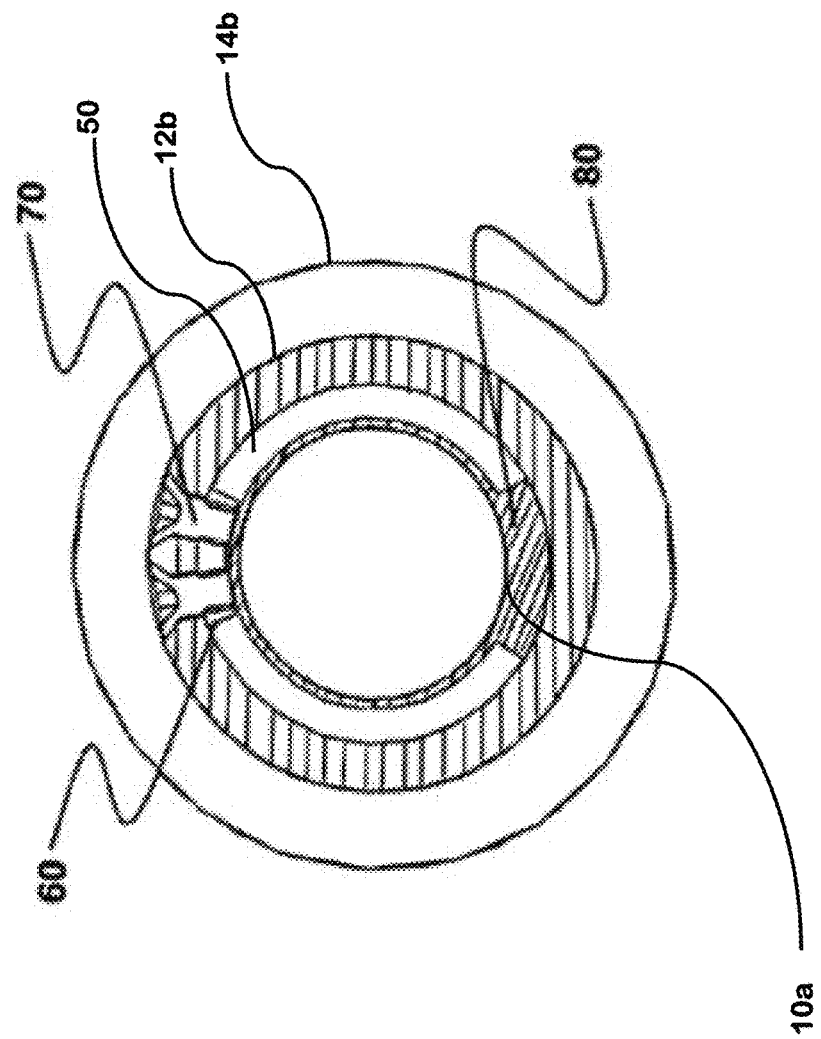
FIG. 4 shows a cross-sectional view of the supply cable and the coupling of the supply cable, in accordance with an embodiment of the present specification.

FIG. 3 shows a perspective view of a portion of section 10a of supply cable 10 shown in FIGS. 2A and 2B. FIG. 4 shows a cross-sectional view of the portion of section 10a shown in FIG. 3. As illustrated in FIGS. 2A and 2B, a rotator portion 80 of coupler component 12a comprises a groove 50. Referring simultaneously to FIGS. 2A, 2B, 3 and 4, a carriage 60, as shown in FIG. 3, is introduced into groove 50. Carriage 60 can move along the length of groove 50. Groove 50 thus acts as a "track" for carriage 60 and is placed within rotator portion 80, which is shaped like a pipe, enabling a 360 degree rotation of carriage 60.

Carriage 60 comprises at least one threaded hole or hollow section 62 for connection with the first end of the coupler component 12b of the coupling fastener 40 by means of screws 70. In an embodiment, carriage 60 comprises two or more than two threaded holes or hollows for connecting with the first end of coupler component 12b.

In an embodiment, the screws 70 are inserted radially into the carriage 60 through openings provided in the wall of the coupler component 12b (not shown in the figures) and fastened to threaded holes 62 provided in the carriage 60. The insertion of the screws 70 ensures a secure connection between the cable sections 10a and 10b via the coupling fastener 40.

The mobility of carriage 60, and therefore the rotation of the two sections 10a, 10b of the supply cable 10 relative to each other, is, in one embodiment, limited to an angle less than 360° by one or more limitation mechanisms. In an embodiment, groove 50 does not run along the complete circumference of the periphery of the coupler component 12a. In an embodiment, groove 50 runs along only a portion of the circumference of coupler component 12a and hence, comprises at least two edges having walls marking an end of groove 50. Carriage 60, during rotation along the track formed by groove 50, is stopped by the walled edges, thereby preventing carriage 60 from moving about the entire circumference of coupler component 12b, and as a result limiting the rotation of section 10a relative to section 10b to a maximum of 180 degrees.

In various embodiments, coupling fastener 40 may comprise covers and seals, such as covers 14a and 14b and o-ring seals 202 and 204 that protect coupling fastener 40 against harmful external influences such as moisture or dust.

In an embodiment, the first o-ring 202 comprises an internal metallic layer enabling an increase in conductivity efficiency of o-ring 202.

In various embodiments, coupling fastener 40 divides supply cable 10 into sections 10a and 10b. In an embodiment, in order to maintain the continuation/succession of electromagnetic shielding along the two sections 10a and 10b, coupler components 12a and 12b are made of metal and are soldered respectively onto sections 10a and 10b.

FIG. 5 shows a cross-sectional view through a coupler component of a supply cable, in accordance with another embodiment of the present specification. As shown in the figure, a supply cable is divided into two sections 510a and 510b which are coupled together by means of coupling fastener 540. The coupling fastener 540 comprises a first coupler component 512a and a second coupler component 512b. FIG. 5 shows a first end of the first coupler component 512a coupled with a proximal end of the section 510a.

In the embodiment shown, the first and second coupler components 512a, 512b are shaped like a pipe. A second end of the first coupler component 512a is coupled with a first end of the second coupler component 512b, while a second end of the second coupler component 512b is coupled with a proximal end of the section 510b. In an embodiment, the diameter of the first end of the second coupler component 512b is larger than that of the second end of the first coupler component 512a, so that the second end of the first coupler component 512a can be pushed into the first end of the second coupler component 512b.

Further, a groove 550 is drilled in at least a portion of the periphery of coupler component 512a. The groove 550 is placed in a rotator portion 580 of the coupling fastener 540. The rotator portion 580 is shaped like a pipe and is, in one embodiment, concentric to coupler component 512a.

To protect the coupling fastener 540 during cleaning processes and to maintain the integrity of the coupling fastener 540, a cover 514a, typically made of a material such as plastic, is fixed onto at least a portion of section 510a and the first end of coupler component 512a, as shown in the figure. Similarly, a cover 514b, typically made of a material such as plastic is fixed onto at least a portion of the section 510b, the second end of the coupler component 512b and a portion of the cover 514a, as shown in the figure. In an embodiment, the ends 501, 502, 503 and 504 of the covers 514a and 514b are glued on to the sections 510a and 510b, as shown, in order to prevent contaminating materials from entering the coupling fastener 540. In another embodiment, the ends 501, 502, 503 and 504 of the covers 514a and 514b maybe fixedly attached to the sections 510a and 510b by using any suitable means of attachment preventing contaminating materials from entering the coupling fastener 540.

Further, as shown, a first o-ring 505 is positioned near a proximal end of the section 510b and a second o-ring 506 is positioned near the point of contact 520 of the cover 514b with the cover 514a, so that groove 550 is positioned between the two o-rings 505 and 506. However, the distance between the o-ring 506 and the groove 550 is greater than the distance between the o-ring 505 and the groove 550.

In various embodiments, the position of the o-rings is changed from the location as illustrated in FIG. 2B to the location as illustrated in FIG. 5 in order to achieve a minimum standard of reprocessing/cleaning with respect to the endoscope employing the present specification. The location of the second o-ring 506 near the point of contact 520 of the cover 514b with the cover 514a, reduces the amount of contaminants that may enter the endoscope from a gap remaining between the cover 514a and section 512a (marked as region 520 in FIG. 5). Reduction in amount of contaminants entering the endoscope leads to a reduction in the amount of cleaning agents/materials required during a cleaning/reprocessing procedure of the endoscope, thereby increasing the efficiency of the cleaning/reprocessing procedure.

The groove 550 is drilled in at least a portion of the periphery of coupler component 512a. Groove 550 is placed in a rotator portion 580, which is shaped like a pipe running along an outer periphery of coupler component 512a, and enables a 360 degree rotation of a carriage (not shown in the figure) placed in the groove 550. In an embodiment, groove 550 does not run around the complete circumference of the section 510a coupled with the coupling fastener 540, thereby providing an end edge for stopping the carriage from moving about the entire circumference. Groove 550 runs along only a portion of the circumference of coupler component 512a and hence, comprises at least two edges having walls marking an end of groove 550. Carriage 60, during rotation along the track formed by groove 50, is stopped by the walled edges, thereby preventing carriage 60 from moving about the entire circumference of coupler component 512b, and as a result limiting the rotation of section 510a relative to section 510b to a maximum of 180 degrees.

The O-rings 505 and 506 are used as seals in the coupling fastener 540 as the o-ring seals allow for a high local stress, and thus, are capable of supporting a high pressure environment. In the embodiment shown in FIG. 5, a groove 507 is located between the second o-ring 506 and the groove 550 at an outer diameter of section 510a. A greasing material may be applied within groove 507 for lubricating portions of coupling fastener 540, thereby facilitating smoother rotation of section 510a relative to section 510b, or vice versa. Such smoother rotation causes a reduction in the pressure that an operating physician is required to apply for maneuvering the endoscope while performing a medical procedure.

Hence, the present specification provides a method of subdividing the supply cable by means of a coupling into two sections that can be rotated relative to each other. This arrangement enables an operator to operate the endoscope comfortably without feeling torsional stress from the supply cable.

The device and method of the present specification does not require any design changes to be made to the control unit of the endoscope with which the supply cable is coupled.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

In the description and claims of the application, each of the words "comprise" "include" and "have", and forms thereof, are not necessarily limited to members in a list with which the words may be associated.

We claim:

1. An endoscope system comprising an endoscope, a main controller, and a supply cable adapted to connect the endoscope to the main controller, the supply cable comprising: a first section, wherein the first section has a first end and a second end, the second end configured to attach to the main controller; a second section, wherein the second section has a first end configured to attach to the endoscope, and a second end; a coupling element for connecting the first end of the first section with the second end of the second section, wherein the coupling element is configured to enable the first section to rotate relative to the second section and wherein the coupling element further comprises: a first coupling component attached to the first end of the first section; a second coupling component attached to the second end of the second section; a groove extending around at least a portion of an outer periphery of one of the first coupling component and the second coupling component, the groove including at least one planar radially-extending surface; a carriage configured to be movable in said groove, wherein the carriage is coupled to the other of the first coupling component and the second coupling component, the carriage includes at least one planar surface facing the at least one planar radially-extending surface of the groove; and a fastening mechanism fastened to the carriage.

2. The endoscope system as claimed in claim 1 wherein the first and the second coupling components are cylindrical in shape.

3. The endoscope system as claimed in claim 1 wherein a diameter of a portion of the second coupling component is greater than a diameter of a portion of the first coupling component, the first and the second coupling components being coupled by inserting said portion of the first coupling component into said portion of the second coupling component.

4. The endoscope system as claimed in claim 1 wherein the fastening mechanism is inserted radially into at least one of the first and second coupling components through one or more openings in a wall of at least one of the first and second sections of the supply cable and fastened to one or more threaded holes in the carriage.

5. The endoscope system as claimed in claim 1 further comprising an abutment that limits an angle of rotation of the first and the second sections of the supply cable relative to each other by abutting the carriage.

6. The endoscope system as claimed in claim 1 wherein the coupling element further comprises a first o-ring seal and a second o-ring seal placed in alignment with a gap separating the first and the second o-ring seals, the first and the second o-ring seals enabling the first and the second sections of the supply cable to be rotatably connected while preventing contaminants from entering the endoscope.

7. The endoscope system as claimed in claim 1 wherein the coupling element and at least a portion of the first and second sections of the supply cable are covered with a cover for preventing contaminants from entering the endoscope.

8. An endoscope system comprising an endoscope, a main controller, and a supply cable adapted to connect the endoscope to the main controller, the supply cable comprising:
a first section, wherein the first section has a first end and a second end, the second end configured to attach to the main controller;
a second section, wherein the second section has a first end configured to attach to the endoscope, and a second end;
a coupling element for connecting the first end of the first section with the second end of the second section, wherein the coupling element is configured to enable the first section to rotate relative to the second section, and wherein the coupling element further comprises:
a first coupling component attached to the first end of the first section;
a second coupling component attached to the second end of the second section;
a recess extending around at least a portion of an outer periphery of one of the first coupling component and the second coupling component;
a slide member configured to be slideably received in said recess, wherein the slide member is coupled to the other of the first coupling component and the second coupling component; and
a fastening element configured to couple the other of the first coupling component and the second coupling component to the slide member.

9. An endoscope system as in claim 8, wherein the slide member includes at least one threaded hole.

10. An endoscope system as in claim 8, wherein the slide member includes at least one radially-extending through-hole.

11. An endoscope system as in claim 8, wherein the fastening element is a screw.

12. An endoscope system as in claim 8, further comprising:
a first cover attached to the first end of the first section of the supply cable; and
a second cover attached to the second end of the second section of the supply cable;
wherein the second cover is configured to receive the first cover.

13. An endoscope system as in claim 8, wherein the carriage includes a curved radially-outward-facing side surface.

14. An endoscope system comprising an endoscope, a main controller, and a supply cable adapted to connect the endoscope to the main controller, the supply cable comprising: a first section, wherein the first section has a first end and a second end, the second end configured to attach to the main controller; a second section, wherein the second section has a first end configured to attach to the endoscope, and a second end; a coupling element for connecting the first end of the first section with the second end of the second section, wherein the coupling element is configured to enable the first section to rotate relative to the second section and wherein the coupling element further comprises: a first coupling component attached to the first end of the first section; a second coupling component attached to the second end of the second section; a groove extending around at least a portion of an outer periphery of one of the first coupling component and the second coupling component, the groove including at least one axially-facing sidewall; and a slide member configured to be slidable in said groove, wherein the slide member is coupled to the other of the first coupling component and the second coupling component, and the slide member includes at least one axially-facing sidewall, and wherein the at least one axially-facing sidewall of the slide member slidably contacts the at least one axially-facing sidewall of the groove; at least one fastening element configured to couple the other of the first coupling component and the second coupling component to the slide member.

15. An endoscope system as in claim 14, wherein the carriage includes a curved radially-outward-facing side surface.

16. An endoscope system as in claim 14, wherein the axially-facing sidewall of the slide member is planar.

17. An endoscope system as in claim 14, further comprising:
   a first cover attached to the first end of the first section of the supply cable; and
   a second cover attached to the second end of the second section of the supply cable;
   wherein the second cover is configured to receive the first cover.

18. An endoscope system as in claim 14, wherein the groove includes two axially-facing sidewalls;
   wherein the slide member includes two axially-facing sidewalls; and
   wherein the two axially-facing sidewalls of the slide member slidably contact the two axially-facing sidewalls of the groove.

\* \* \* \* \*